(12) United States Patent
Kim et al.

(10) Patent No.: US 11,286,516 B2
(45) Date of Patent: Mar. 29, 2022

(54) METHOD FOR RAPID DESIGN OF VALID HIGH-QUALITY PRIMERS AND PROBES FOR MULTIPLE TARGET GENES IN QPCR EXPERIMENTS

(71) Applicant: Daegu Gyeongbuk Institute of Science and Technology, Daegu (KR)

(72) Inventors: Min Soo Kim, Daegu (KR); Hyerin Kim, Daegu (KR); Jaehyung Koo, Daegu (KR); Na Na Kang, Daegu (KR); KyuHyeon An, Gyeonggi-do (KR)

(73) Assignee: Daegu Gyeongbuk Institute of Science and Technology, Daegu (KR)

( * ) Notice: Subject to any disclaimer, the term of this patent is extended or adjusted under 35 U.S.C. 154(b) by 473 days.

(21) Appl. No.: 15/497,244

(22) Filed: Apr. 26, 2017

(65) Prior Publication Data

US 2017/0369934 A1 Dec. 28, 2017

(30) Foreign Application Priority Data

Jun. 28, 2016 (KR) ........................ 10-2016-0080872

(51) Int. Cl.
| | |
|---|---|
| *C12Q 1/6811* | (2018.01) |
| *G16B 35/00* | (2019.01) |
| *G16C 20/60* | (2019.01) |
| *G16B 20/00* | (2019.01) |
| *G16B 25/00* | (2019.01) |
| *G16B 30/10* | (2019.01) |
| *G16B 20/20* | (2019.01) |
| *G16B 30/00* | (2019.01) |

(52) U.S. Cl.
CPC ............ *C12Q 1/6811* (2013.01); *G16B 20/00* (2019.02); *G16B 20/20* (2019.02); *G16B 25/00* (2019.02); *G16B 30/10* (2019.02); *G16B 35/00* (2019.02); *G16C 20/60* (2019.02); *G16B 30/00* (2019.02)

(58) Field of Classification Search
CPC ...... C12Q 1/6811; G16C 20/60; G16B 35/00; G16B 30/00; G16B 20/00
See application file for complete search history.

(56) References Cited

PUBLICATIONS

Kim, MRPrimer: a MapReduce-based method for the thorough design of valid and ranked primers for PCR, Jun. 24, 2015, Nucleic Acids Research, 43(20), pp. 1 to 10 (Year: 2015).*
MapReduce Tutorial, Feb. 26, 2015, The Apache Software Foundation, pp. 1-42 (Year: 2015).*
Rozen, Primer3 on the WWW for General Users and for Biologist Programmers, 1999, Bioinformatics Methods and Protocols. Methods in Molecular Biology, 132, pp. 365 to 386 (Year: 1999).*
Rodrizuez-Tome, Resources at EBI, Methods in Molecular Biology, 1999, Methods in Molecular Biology, 132, pp. 313 to 335 (Year: 1999).*
Misener, Bioinformatics Methods and Protocols, 1999, Methods in Molecular Biology, 132, pp. 1 to 500 (Year: 1999).*
Smith, Advantages and limitations of quantitative PCR (Q-PCR)-based approaches in microbial ecology, Dec. 2008, FEMS Microbial Ecol, 67, pp. 6 to 20 (Year: 2008).*
Pattyn et al., RTPrimerDB: the Real-Time PCR primerand probe database, 2003, Nucleic Acids Research, 31(1), p. 122-123 (Year: 2003).*
Kim et al., "MRPrimerW: a tool for rapid design of valid high-quality primers for multiple target qPCR experiments", Nucleic Acids Research Advance Access, May 6, 2016, 8 pages.

* cited by examiner

*Primary Examiner* — Olivia M. Wise
*Assistant Examiner* — Kaitlyn L Minchella
(74) *Attorney, Agent, or Firm* — Hauptman Ham, LLP

(57) ABSTRACT

Disclosed is a method of designing a valid primer pair satisfying a specificity condition. The method includes searching for an identifier of a base sequence from a genetic information index based on a query language associated with a gene, searching for a candidate primer from a provided candidate primer set index to satisfy the specificity condition based on the identifier of the base sequence, filtering the candidate primer based on primer-related filtering conditions, and providing information about a primer pair satisfying the query language and the filtering conditions based on a result of the filtering.

17 Claims, 17 Drawing Sheets

FIG. 4A

| | key | value |
|---|---|---|
| 401 | Species:Accession:$accession_0$ | sid |
| | ⋮ | |
| | Species:Accession:$accession_n$ | sid |
| 402 | Species:CCDSID:$ccdsID_0$ | sid |
| | ⋮ | |
| | Species:CCDSID:$ccdsID_m$ | sid |

FIG. 5A

| key | value | | | |
|---|---|---|---|---|
| Species:sidset$_1$+len(*) | (p+sid+pos)[0] | 1 | (p+sid+pos)[1] | ... |

| key | value | | | | |
|---|---|---|---|---|---|
| Species:taqman+sidset$_1$ | (probe+sid+pos)[0] | 1 | (probe+sid+pos)[1] | ... | ⟵ 502 |
| ⋮ | | | | | |

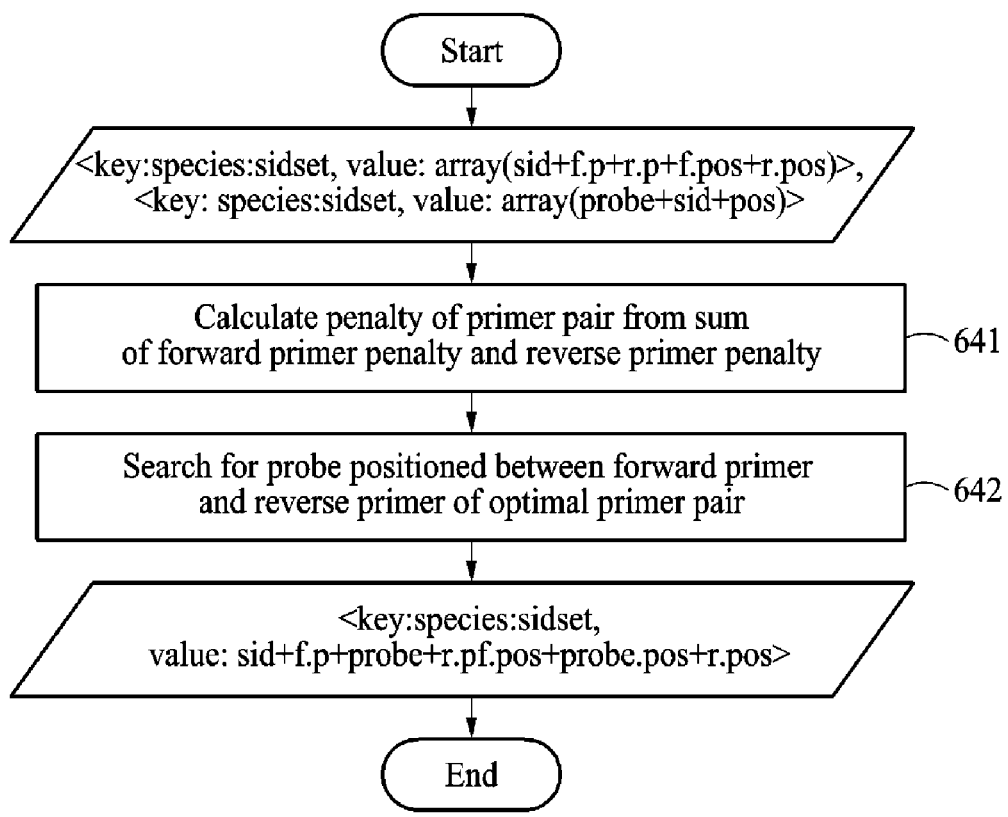

[B] Less target-specific primer pairs
>Total number of target gene(s): 2

| No. | Gene symbol | Accession number | Penalty score | Forward primer | | | Reverse primer | | | Forward TM | Reverse TM | Amplicon size | Forward position | Reverse position |
|---|---|---|---|---|---|---|---|---|---|---|---|---|---|---|
| 1 | TP53<br>TP53<br>TP53<br>TP53 | NM_002346.3<br>NM_001126112.2<br>NM_001276697.1<br>NM_001126115.1<br>NM_001126118.1<br>NM_001276760.1<br>NM_001276761.1 | 7.717 | ... | T | G | ... | T | T | 60.00 | 59.29 | 101<br>101<br>101<br>101 | 1042<br>563<br>846<br>925 | 1142<br>663<br>946<br>1025 |
| 2 | A1CF<br>A1CF | NM_138933.2<br>NM_001198820.1<br>NM_001198819.1 | 11.73 | ... | CA | T | ... | T | TG | 60.08 | 58.44 | 106<br>106 | 29<br>29 | 134<br>134 |

FIG. 10C

▲ No primers due to too strict parameters
> Total number of target gene(s): 2

| No. | Gene symbol | Accession number | Parameter | Current value | Suggested value |
|-----|-------------|------------------|-----------|---------------|-----------------|
| 1 | UBE2J2 | NM_058167.2 | Self-complementarity Max | 5 | 8 |
| 2 | HES4 | NM_021170.3 | Hairpin Max | 3 | 4 |

✓ Please adjust the filtering parameters using the above suggested values and then resubmit the query.

FIG. 10D

▲ No primers due to too strict parameters
>Total number of target gene(s): 2

No primer pair is found forthdp1, kfk2

✓ Make sure that "Species" and "Search by" are selected correctly.
✓ Make sure that keywords are spelled correctly

METHOD FOR RAPID DESIGN OF VALID HIGH-QUALITY PRIMERS AND PROBES FOR MULTIPLE TARGET GENES IN QPCR EXPERIMENTS

CROSS-REFERENCE TO RELATED APPLICATION(S)

This application claims the priority benefit of Korean Patent Application No. 10-2016-0080872 filed on Jun. 28, 2016, in the Korean Intellectual Property Office, the disclosure of which is incorporated herein by reference for all purposes.

BACKGROUND

1. Field

One or more example embodiments relate to a method of rapidly and simultaneously designing a valid primer set and a valid probe set that satisfy specificity conditions to detect multiple target genes.

2. Description of Related Art

In general, a polymerase chain reaction (PCR) is technology for rapidly amplifying a deoxyribonucleic acid (DNA) sequence. The PCR, which is standard technology, is used in various fields of applications, such as, for example, a phylogenetic analysis, a genetic test, and a DNA cloning. A quantitative PCR (qPCR), also known as a realtime PCR, in particular, is mainly used to verify a change in expression of multiple target genes and screen high-throughput experiment results.

FIG. 1 illustrates a general state in which a forward primer, a reverse primer, and a probe are bound with a target sequence. Referring to FIG. 1, in each of split DNA strands 202, a forward primer 205 and a probe 208 are bound with a reverse target template 207, and a reverse primer 203 is bound with a forward target template 201 to synthesize a DNA polymerase.

As illustrated in FIG. 1, while a forward primer is being synthesized in a direction of 5' to 3', a probe corresponding to a target may be degraded into small fragments and reveal an attached fluorescent material.

To achieve a best result in all PCR experiments, an optimal primer needs to be designed.

In a case of manually designing a primer, a great amount of time may be consumed and numerous restrictions or conditions (hereinafter referred only to as conditions) may need to be considered simultaneously, and thus it may be prone to obtain an erroneous result.

A homology test, which needs to be additionally and essentially considered, is performed to verify whether a designed primer is attached only to a target sequent without being attached to a non-target sequence, and an additional tool, such as, for example, a basic local alignment search tool (BLAST), has hitherto been used for such a test.

Thus, rapidly and automatically designing a high-quality primer that satisfies the numerous conditions and the homology test has remained as a challenging issue yet to be solved. In particular, simultaneously designing multiple primers that satisfy strict conditions for the qPCR is even more challenging.

In the qPCR, a method of detecting a target sequence of a probe along with a primer is used to improve an experimental specificity. Although a probe may improve a specificity greatly, designing it along with a primer may be more complicated, and thus a greater attention needs to be paid.

Recently, many websites that aid in primer designing for PCR experiments have been developed. For example, Primer3Plus is a most widely used tool through which a user may change a condition for a target sequence.

For another example, BatchPrimer3 to which a main algorithm of Primer3 is applied may enable primer designing through an alignment method for multiple target genes. However, the aforementioned two websites do not perform the homology test on non-target sequences, and thus a user needs to conduct the homology test on each of candidate primers using an additional aligning or sorting tool.

In contrast, Primique performs the homology test, within a restricted range, on non-target sequences uploaded by a user, using the BLAST. Due to a high calculative overhead of the homology test, a maximum size of a non-target sequence database (DB) that may be uploaded by a user is 10 megabits (MB) and such a size may not include an entire genome sequence DB, and thus Primique may have a limitation in designing a high-quality primer.

In addition, QuantPrime also performs the homology test on a candidate primer designed using a Primer 3 algorithm and whole transcriptome or genome database, using the BLAST. The aforementioned two websites perform the homology test based on a local alignment algorithm.

However, such a local alignment-based heuristic approach may not correctly count the number of mismatches between a primer and a non-target sequence. Thus, the aforementioned methods may design a suboptimal primer pair.

In contrast, Primer-BLAST performs the homology test using a global alignment algorithm, and thus may verify a complete alignment between a primer and a target.

Thus, the Primer-BLAST outputs a target-specific primer pair. Although the Primer-BLAST exhibits a higher performance in the homology test, it performs the alignment or the sorting based on specificity, not on a primer quality. In addition, due to a high calculative overhead to obtain a more accurate result of the homology test, the Primer-BLAST does not support an alignment design for the qPCR for multiple targets.

In addition, there are also websites, for example, PrimerBank, RTPrimerDB, and qPrimerDepot, which provide a search from a predesigned primer DB, rather than designing a primer in real time based on a query from a user. Among these websites, the PrimerBank is a largest primer DB that has been updated over past years. The PrimerBank may be effective in a realtime PCR experiment because specificity of primers of the PrimerBank is experimentally verified under a same condition. The PrimerBank provides a predesigned primer, and thus a user may not change a condition. However, changing a condition may be essential in a qPCR experiment that requires a set of complete primer pairs that satisfy a same condition.

SUMMARY

An aspect provides a method of simultaneously and rapidly designing a valid primer set and a valid probe set that satisfy a specificity condition to detect multiple target genes.

In related arts, an additional tool, for example, a basic local alignment search tool (BLAST), is used for a homology test for a non-target sequence, the method may extract a candidate primer set and a candidate probe set that satisfy a specificity condition for all possible gene pairs through a Hadoop-based offline operation.

Regarding an alignment design in related arts, the method may build, in a memory, indexes of the candidate primer set and the candidate probe set satisfying the specificity condition for multiple target genes input by a user, and rapidly search for and design a primer and a probe through an online operation.

In addition, dissimilar to the PrimerBank that provides predesigned primers under a same condition, the method may newly perform an online operation each time a user changes a condition and enable the user to obtain a desired high-quality primer set.

In related arts, a great attention needs to be paid to design a primer and a probe simultaneously. The method may configure an index in a memory by obtaining a probe set satisfying specificity and conditions, and obtain a probe along with a primer satisfying a query from a user.

The method may be a web-based method that may simultaneously and rapidly design a valid primer set and a valid probe set satisfying a specificity condition to detect multiple target genes.

The method may extract all candidate primer sets and probe sets satisfying a specificity condition for all possible gene pairs through a Hadoop-based offline operation, without using an additional tool, such as, for example, the BLAST, for the homology test for a non-target sequence. In actuality, the method designs 165,923,450 primers and 176,039,685 primers that may amplify sequences by 99% for 31,394 pieces of human consensus coding sequence (CCDS) data and 24,833 pieces of mouse CCDS data, respectively.

In addition, the method may build, in the memory, an index of a valid primer set and probe set satisfying the specificity condition to enable a user to rapidly search for multiple target genes input by the user.

Further, the method may perform an online operation anew each time a user changes a condition to enable the user to obtain a desired high-quality primer set.

Furthermore, the method may obtain a probe set satisfying specificity and a condition, along with a primer pair satisfying a query from a user, to improve specificity associated with an amplification of a target sequence.

According to an aspect, there is provided a method of simultaneously designing a valid primer set and a valid probe set that satisfy a specificity condition to detect multiple target genes. The method may include a first stage of extracting a candidate primer set and a candidate probe set that satisfy a specificity condition for all possible gene pairs through a Hadoop-based offline operation for a massive deoxyribonucleic acid (DNA) sequence database (DB), a second stage of configuring, in a memory, an index to perform a specificity test using the candidate primer set and the candidate probe set that are extracted from the first stage, and a third stage of selecting an optimal primer pair and an optimal probe for each target gene and outputting the selected primer pair and probe to a webpage after rapidly searching for a valid primer set and a valid probe set satisfying single and/or pair filtering conditions based on which each of multiple target genes given by a user is detected, through an online operation using the index configured in the second stage.

The first stage may include extracting a candidate primer set satisfying an applied minimum number of filtering conditions from the massive DNA sequence DB through a Hadoop distribution algorithm, extracting a candidate probe set satisfying an applied minimum number of filtering conditions from the massive DNA sequence DB through the Hadoop distribution algorithm, and extracting a candidate passing a homology test from all extracted candidate primer and probe sets. Here, the homology test may be performed to compare all the extracted candidate primer and probe sets to non-target sequences through the Hadoop distribution algorithm and remove, from all the extracted candidate primer and probe sets, a candidate having a 5' end with four or less mismatches and having a remaining similar 3' end or a candidate only having two or less mismatches.

The second stage may include generating a genetic information index based on a characteristic of gene information, generating a candidate primer set index using the extracted candidate primer set and a candidate probe set index using the extracted candidate probe set, and a cache primer pair index, and uploading, to the memory, the generated genetic information index, the generated candidate primer set index and the generated candidate probe set index, and the generated cache primer pair index.

The genetic information index may include a two hash-structured index including unique gene information such as a GenBank accession number and a consensus coding sequence (CCDS) identification (ID) of National Center for Biotechnology Information (NCBI) (NCBI CCDS ID), a four list-structured index including duplicated gene information such as an NCBI gene symbol, an NCBI gene ID, a GenBank alias, and a keyword, and a single list-structured index including all the gene information.

The candidate primer set index may be a hash-structured index including a key field and a value field. The key field may be in a form of species:sidset+len(*) in which len denotes a primer length and * denotes a reverse primer, and the value field may be in a form of primer+sid+pos including a primer sequence and position information (pos).

The cache primer pair index may be a hash-structured index including top primer pairs calculated in advance with respect to each target sequence, and may include a key and a value. The key and the value may be arranged in a form of species:top:sidset and in a form of sid+f.p+r.p+f.pos+r.pos, respectively.

The third stage may include 3-1 stage of processing a gene-related query input by the user, fetching and outputting a candidate from the cache primer pair index in response to values of the filtering conditions being a default value, and removing a candidate not satisfying single filtering conditions applied by the user while searching for a primer and a probe from the candidate primer set index and the candidate probe set index, 3-2 stage of designing a primer pair by applying pair filtering conditions given by the user using primers passing the previous stage, and 3-3 stage of calculating a penalty of each of primer pairs passing the pair filtering conditions and outputting, to a webpage, top primer pairs having a highest penalty in a same sidset group along with a probe satisfying a corresponding position condition.

In the third stage, 3-1 stage may include removing a primer not satisfying the single filtering conditions given by the user by verifying in order a length, a temperature, a guanine-cytosine (GC) content, a self-complementarity, a 3' end self-complementarity, consecutive bases, an end stability, and a hairpin of the single filtering conditions.

In the third stage, 3-2 stage may include removing a primer not satisfying the pair filtering conditions by verifying in order a temperature difference, a length difference, a generated product length, a pair-complementarity, and a 3' end pair-complementarity of the pair filtering conditions.

In the third stage, 3-3 stage may include calculating, as the penalty of each of the primer pairs passing a pair filtering process, a sum of a forward primer penalty and a reverse primer penalty of each of the primer pairs, and outputting the top primer pairs in the same sidset group having the highest penalty to the webpage along with the probe satisfying the position condition in response to the penalty being calculated for each of the primer pairs.

The outputting to the webpage in 3-3 stage may include outputting probes and top primer pairs to be attached to a single target sequence and satisfying the single and/or pair filtering conditions input by the user, outputting top primer pairs to be attached to multiple target sequences and satisfying the single and/or pair filtering conditions input by the user, outputting queries based on which searches for primer pairs satisfying the single and/or pair filtering conditions input by the user are not performed, and outputting queries based on which searches for valid candidate primers are not performed due to the valid candidate primers not being in the candidate primer set index.

In response to a presence of the probes and the top primer pairs to be attached to the single target sequence and satisfying the single and/or pair filtering conditions input by the user, the outputting to the webpage in 3-3 stage may include providing gene information, a primer pair sequence, a probe sequence, a temperature, an amplicon size, and a position. In response to a presence of the top primer pairs to be attached to the multiple target sequences and satisfying the single and/or pair filtering conditions input by the user, the outputting to the webpage in 3-3 stage may include providing gene information, a primer pair sequence, a temperature, an amplicon size, and a position. In response to an absence of a primer pair satisfying the single and/or pair filtering conditions input by the user, the outputting to the webpage in 3-3 stage may include providing gene information, conditions of which a value is to be changed, a value input by the user, and a value to be corrected. In response to an absence of a valid candidate primer due to the valid candidate primer not being in a corresponding index, the outputting to the webpage in 3-3 stage may include providing a query language without a result and a re-search guideline.

In 3-3 stage, in response to the absence of the primer pair satisfying the single and/or pair filtering conditions input by the user and in response to the absence of the valid candidate primer due to the valid candidate primer not being in the corresponding index, the webpage may provide an interactive interface to obtain an accurate search result by allowing the user to immediately correct a query language and a condition from a result display and perform a re-search using the corrected query language and the corrected condition.

In response to the online operation being completed, a search result may be transmitted to an e-mail address input by the user.

Additional aspects of example embodiments will be set forth in part in the description which follows and, in part, will be apparent from the description, or may be learned by practice of the disclosure.

BRIEF DESCRIPTION OF THE DRAWINGS

These and/or other aspects, features, and advantages of the present disclosure will become apparent and more readily appreciated from the following description of example embodiments, taken in conjunction with the accompanying drawings of which:

FIGS. 4A through 4C are diagrams illustrating an example of a configuration of a genetic information index according to an example embodiment;

FIGS. 5A through 5C are diagrams illustrating an example of a configuration of a candidate primer index, an example of a configuration of a candidate probe index, and an example of a configuration of a cache primer pair index according to an example embodiment;

FIG. 9 is a flowchart illustrating an example of a sorting operation performed in operation 640 of FIG. 6; and FIGS. 10A through 10D are diagrams illustrating examples of output results according to an example embodiment.

DETAILED DESCRIPTION

The following detailed description is provided to assist the reader in gaining a comprehensive understanding of the methods, apparatuses, and/or systems described herein. However, various changes, modifications, and equivalents of the methods, apparatuses, and/or systems described herein will be apparent after an understanding of the disclosure of this application. For example, the sequences of operations described herein are merely examples, and are not limited to those set forth herein, but may be changed as will be apparent after an understanding of the disclosure of this application, with the exception of operations necessarily occurring in a certain order. Also, descriptions of features that are known in the art may be omitted for increased clarity and conciseness.

The features described herein may be embodied in different forms, and are not to be construed as being limited to the examples described herein. Rather, the examples described herein have been provided merely to illustrate some of the many possible ways of implementing the methods, apparatuses, and/or systems described herein that will be apparent after an understanding of the disclosure of this application.

The terminology used herein is for the purpose of describing particular embodiments only and is not intended to be limiting. Terms such as first, second, A, B, (a), (b), and the like may be used herein to describe components. Each of these terminologies is not used to define an essence, order, or sequence of a corresponding component but used merely to distinguish the corresponding component from other component(s). For example, a first component may be referred to as a second component, and similarly the second component may also be referred to as the first component. Also, as used herein, the singular forms "a," "an," and "the," are intended to include the plural forms as well, unless the context clearly indicates otherwise. It will be further understood that the terms "comprises," "comprising," "includes," and/or "including," when used herein, specify the presence of stated features, integers, operations, elements, and/or components, but do not preclude the presence or addition of one or more other features, integers, operations, elements, components, and/or groups thereof.

Hereinafter, a method of simultaneously designing a valid primer set and a valid probe set that satisfy a specificity condition to detect multiple target genes will be described in detail with reference to the accompanying drawings.

Figure 1:
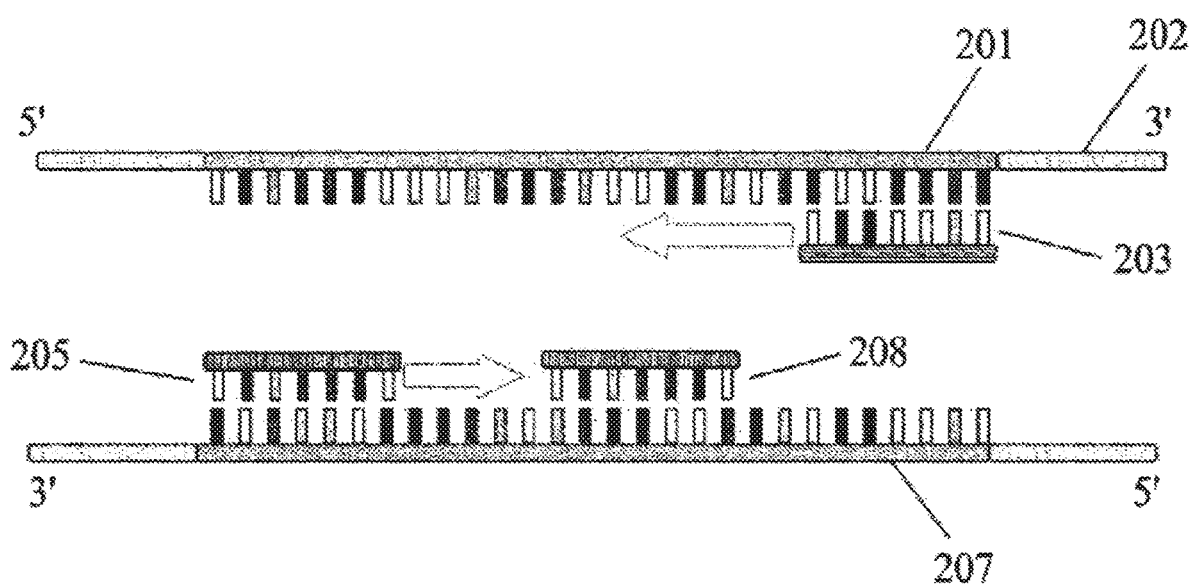
FIG. 1 is a diagram illustrating an example of a general state in which a forward primer, a reverse primer, and a probe are bound with a target sequence.
Figure 2:
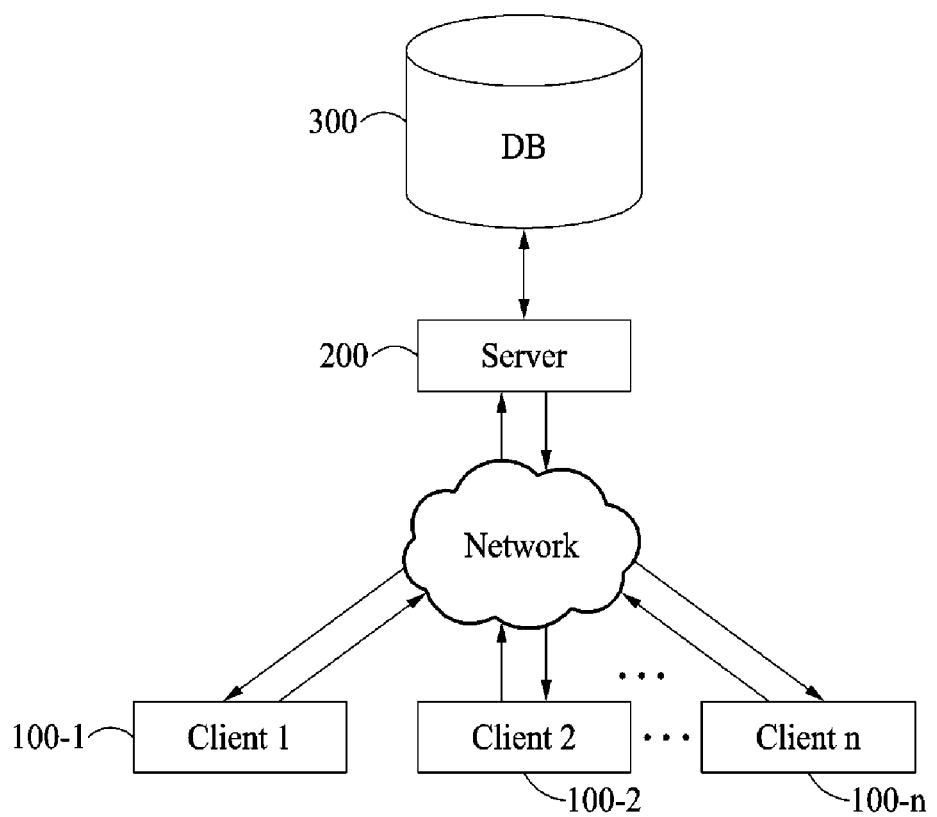
FIG. 2 is a diagram illustrating an example of a configuration of a system according to an example embodiment.

FIG. 2 is a diagram illustrating an example of a configuration of a system according to an example embodiment.

Referring to FIG. 2, a system includes a plurality of clients, for example, client 1 100-1, client 2 100-2, ..., client n 100-n, a server 200, and a database (DB) 300. The server 200 and the clients 100-1, 100-2, ..., 100-n may be connected through a wired network or a wireless network.

When a user of a client of the clients 100-1, 100-2, ..., 100-n inputs a query language and a restriction or a condition (hereinafter only referred to as condition), information about the input query and the input condition may be transmitted to the server 200 through the network.

The server 200 may search for candidate primers suited to the query language transmitted from the clients 100-1, 100-2, ..., 100-n through the network, from an index of the DB 300 through an online operation, and test the retrieved candidate primers based on the condition provided from the clients 100-1, 100-2, ..., 100-n.

A method of configuring the index of the DB 300 will be described hereinafter in detail with reference to FIG. 3.

Figure 3:
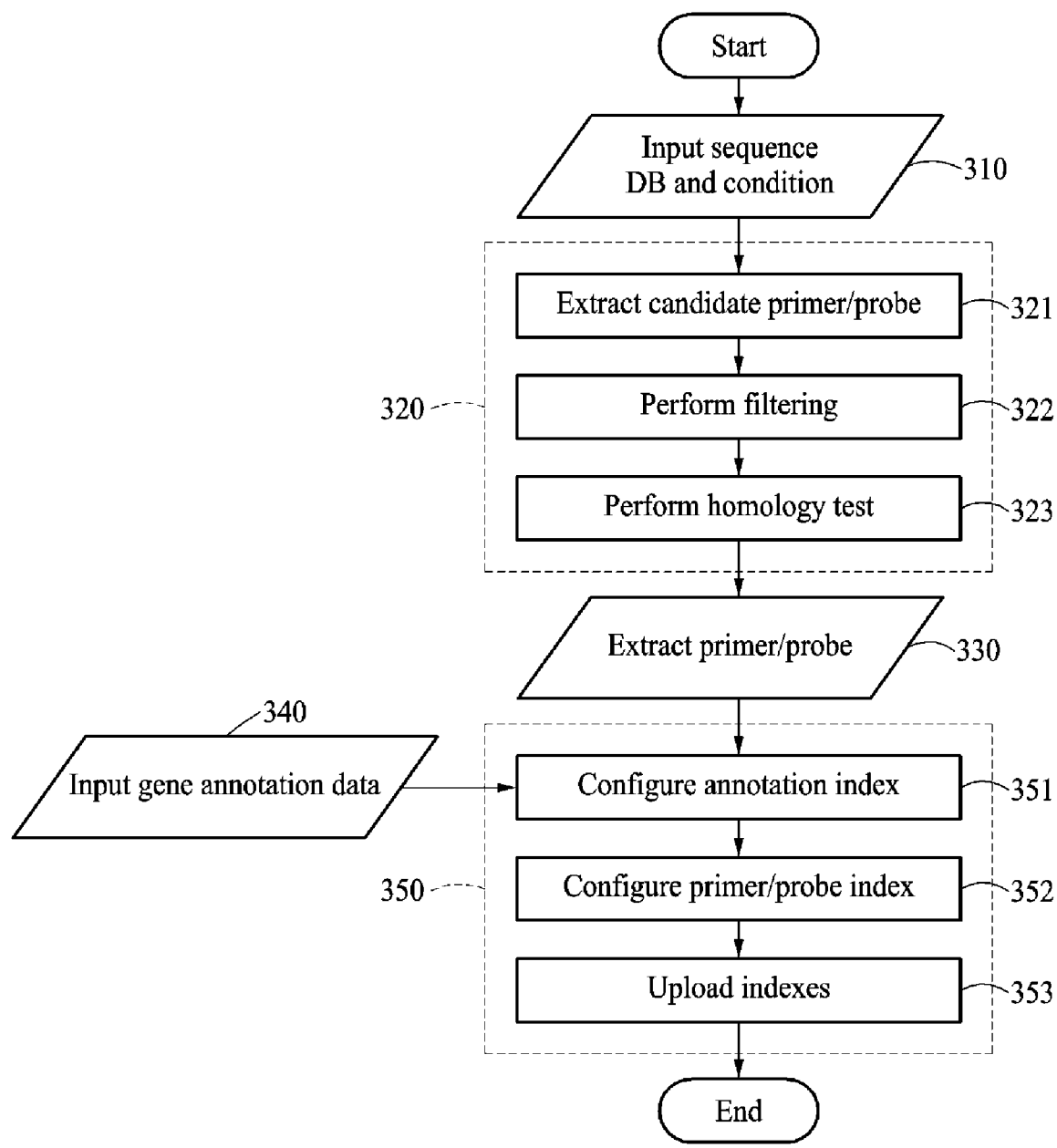
FIG. 3 is a flowchart illustrating an example of a method of configuring an index from which a search for a candidate primer and a candidate probe satisfying a specificity condition is performed in response to a gene-related query according to an example embodiment.

FIG. 3 is a flowchart illustrating an example of a method of configuring an index from which searches for a candidate primer and a candidate probe satisfying a specificity condition is performed in response to a gene-related query according to an example embodiment.

Referring to FIG. 3, in operation 310, a massive deoxyribonucleic acid (DNA) sequence DB and a condition are input. In operation 320, a candidate primer set satisfying a specificity condition for all possible gene pairs is extracted from the input massive DNA sequence DB through a Hadoop-based offline operation. In operation 320, along with the candidate primer set, a candidate probe set satisfying a specificity condition for all possible gene pairs is also extracted through the Hadoop-based offline operation.

In detail, operation 320 includes operation 321 of extracting a candidate primer of partial sequences having all possible lengths between a minimum length (minL) and a maximum length (maxL) from the input massive DNA sequence DB. In operation 321, a candidate probe with all possible lengths is also extracted.

In detail, operation 320 also includes operation 322. In operation 322, a filtering is performed to filter out or remove a candidate primer that does not satisfy applied minimum conditions input in operation 310 from candidate primers extracted in operation 321. In operation 322, a candidate probe that does not satisfy applied probe-related minimum conditions is filtered out or removed from candidate probes extracted in operation 321.

In detail, operation 320 includes operation 323. In operation 323, a homology test is performed based on all candidate primers extracted in operation 321 and candidate primers obtained through the filtering performed in operation 322. For example, in operation 323, the homology test is performed to compare a set of all the candidate primers and a set of all the candidate probes extracted in operation 321 to non-target sequences through a Hadoop distribution algorithm, and remove a candidate having a 5' end with a preset number or greater number (e.g., greater than or equal to 4) mismatches and having a remaining similar 3' portion, or a candidate having a preset number (e.g., greater than or equal to 1 and less than or equal to 2) of mismatches overall. In operation 330, a candidate primer passing the homology test is extracted. According to an example embodiment, the homology test is performed based on all the candidate probes extracted in operation 321 and the candidate probes obtained through the filtering performed in operation 322, and a candidate probe passing the homology test is extracted.

In operation 350, an index structure including a key-value pair is configured in a main memory using the candidate primer extracted in operation 330. In operation 350, an index structure corresponding to the candidate probe is also configured.

In detail, operation 350 includes operation 340 of inputting gene annotation data, and operation 351 of configuring the input gene annotation data as an annotation index.

In detail, operation 350 also includes operation 352 of configuring an index indicating the candidate primer extracted in operation 330, and operation 353 of uploading the indexes configured in operation 351 and 352 to the memory, for example, the DB 300 of FIG. 2. Here, the term "configure" is used with a similar meaning to a term "form" or "build." According to an example embodiment, an index indicating the candidate probe is also configured and uploaded to the memory, or the DB 300. Hereinafter, for convenience of description, examples of using a candidate primer and a candidate probe together will be described. However, changes may be made to such examples, and thus either a candidate primer or a candidate probe may be used.

A structure of the index configured in operation 351 will be described in greater detail with reference to FIGS. 4A through 4C.

Figure 4B:
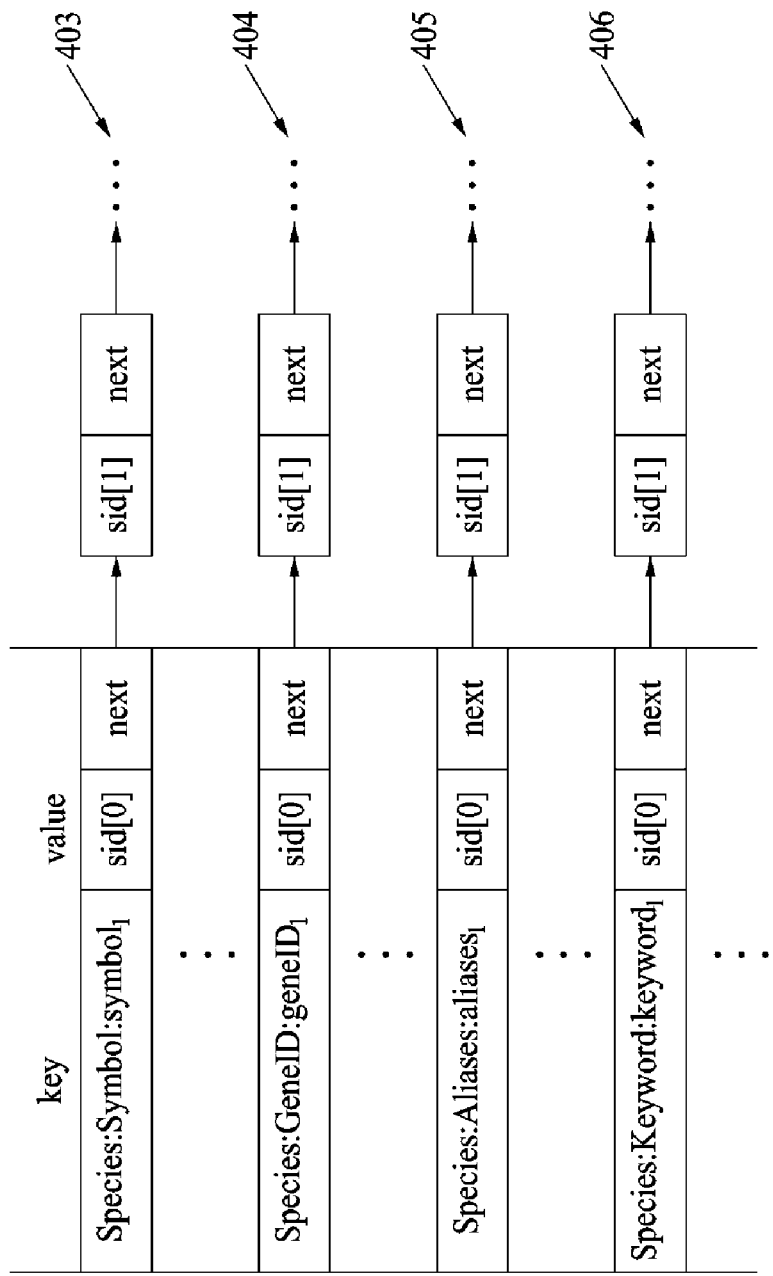
Figure 4C:
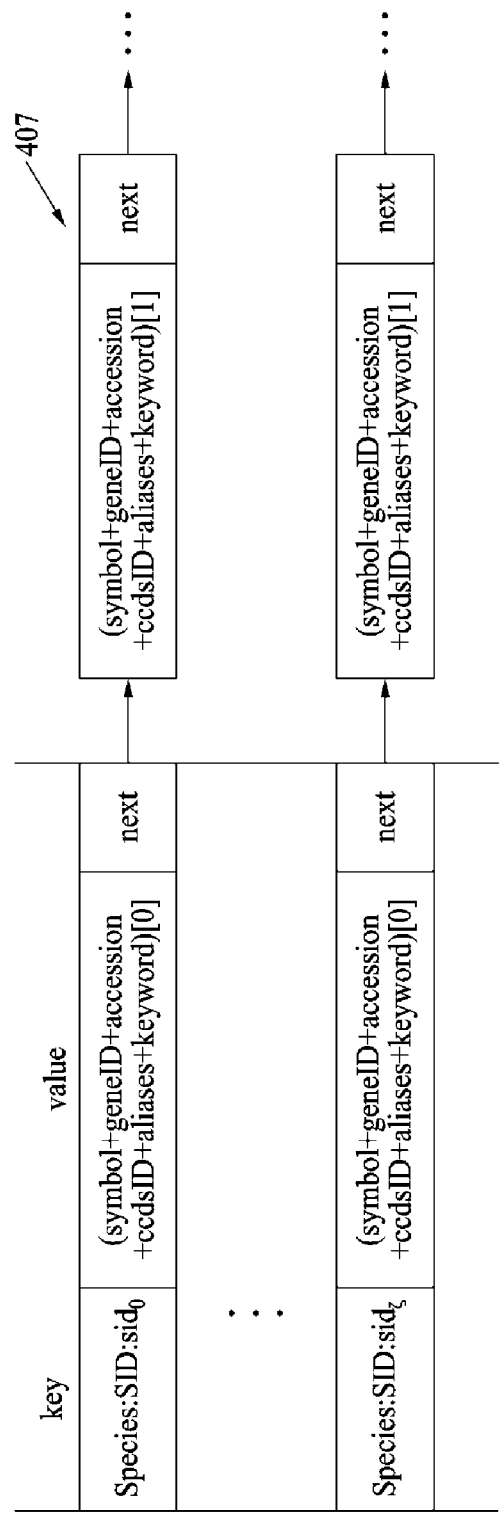

FIGS. 4A through 4C are diagrams illustrating an example of a configuration of a genetic information index according to an example embodiment. A key of the genetic information index is used for matching a query from a user, and a value of the genetic information index indicates a single sequence identification (ID) or includes a sequence ID list. Each sequence ID included in the value corresponds to a key of a primer and/or probe index, or is included in the key of the primer and/or probe index.

Referring to FIG. 4A, a two hash-structured index is configured using a GenBank accession number 401 and a CCDS ID of National Center for Biotechnology Information (NCBI) (NCBI CCDS ID) 402 having unique gene information.

Referring to FIG. 4B, a four list-structured index is configured using an NCBI gene symbol 403, an NCBI gene ID 404, a GenBank alias 405, and a keyword 406 having duplicated gene information.

Referring to FIG. 4C, a single list-structured index 407 having all the gene information is configured. The index 407 may be used to display, on a search result display, information associated with a certain gene.

Hereinafter, a configuration of a primer index and a probe index that are built in operation 352 described with reference to FIG. 3 will be described in detail with reference to FIGS. 5A through 5C.

Figure 5C:
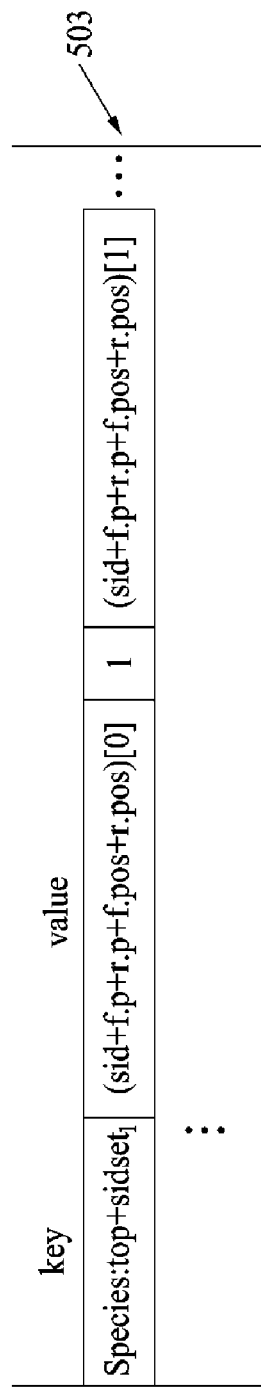

FIGS. 5A through 5C are diagrams illustrating an example of a configuration of a candidate primer set index, an example of a candidate probe set index, and an example of a configuration of a cache primer pair index according to an example embodiment. Although to be described hereinafter, each index includes "sidset" as a key, and information associated with a primer, a probe, or a cache primer pair corresponding to at least one "sid" included in the "sidset" as a value. According to an example embodiment, in addition to the "sidset," each index further includes additional information, for example, species, as the key to improve a search speed.

Referring to FIG. 5A, a candidate primer index 501 is configured as a hash-structured index including a key that is in a form of species:sidset+len(*) in which "len" denotes a primer length and "*" denotes a reverse primer, and a value that is in a form of primer+sid+pos having a primer sequence and position information (pos).

Referring to FIG. 5B, a candidate probe index 502 is configured as a hash-structured index including a key that is in a form of species:taqman:sidset and a value that is in a form of probe+sid+pos having a probe sequence and position information (pos).

Referring to FIG. 5C, a single cache primer pair index 503 is configured as a hash-structured index having top (or highest-rank) primer pairs calculated in advance with respect to each target sequence, and including a key arranged in a form of species:top:sidset and a value arranged in a form of sid+f.p+r.p+f.pos+r.pos.

In a case that a query and a condition are input online from a user of a client, for example, the clients 100-1, 100-2, . . . , 100-n of FIG. 2, when each index is configured through the operations described with reference to FIG. 3 and configured as illustrated in FIGS. 4A through 4C and 5A through 5C, the server 200 of FIG. 2 may perform an online operation and provide a result of searching for a valid primer and a valid probe. Such a process will be described hereinafter in detail with reference to FIG. 6.

Figure 6:
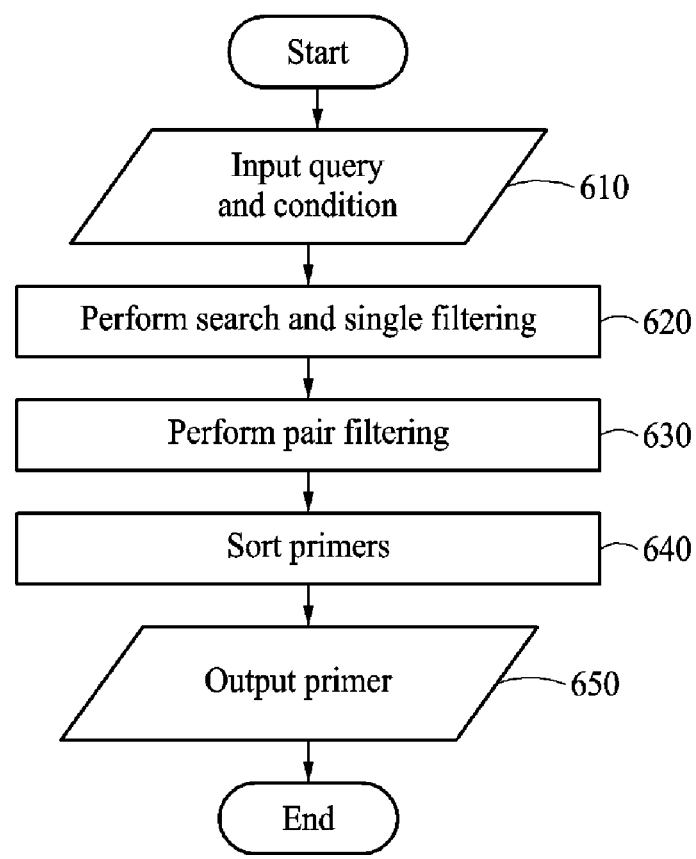
FIG. 6 is a flowchart illustrating an example of a method of designing valid primers using an index according to an example embodiment.

FIG. 6 is a flowchart illustrating an example of a method of designing valid primers using an index according to an example embodiment.

Referring to FIG. 6, in operation 610, a query language and information on a condition are received online as an input from a user, for example, a plurality of clients, through a network. When the query language and the information on the condition are input, the server 200 of FIG. 2 may search for a candidate primer and/or a candidate probe in response to the received query language from the DB 300 of FIG. 2 using the index structure configured through the operations described with reference to FIG. 3. For example, the server 200 searches for at least one sid corresponding to the query language using the annotation index illustrated in FIG. 4A or 4B based on the query language. The server 200 searches for candidate primers corresponding to the retrieved sid using the primer index illustrated in FIG. 5A. For example, the server 200 detects a sidset including the retrieved sid from the primer index illustrated in FIG. 5A, and then searches for stored candidate primers corresponding to the detected sidset. Similarly, the server 200 searches for candidate probes corresponding to the retrieved sid using the probe index illustrated in FIG. 5B.

In operations 620 and 630, the server 200 rapidly searches for a valid primer set and a valid probe set that satisfy the condition provided by the user with respect to the retrieved candidate primer and probe, for example, a single and/or pair filtering condition, to detect each of multiple target genes, and then verifies the condition and designs a probe and primer pair.

In operation 640, the server 200 selects only an optimal primer pair and an optimal probe for each target gene. In operation 650, the server 200 outputs the selected optimal primer pair and the selected optimal probe to a webpage.

Hereinafter, the operations described with reference to FIG. 6 will be described in greater detail with reference to the accompanying drawings.

Figure 7:
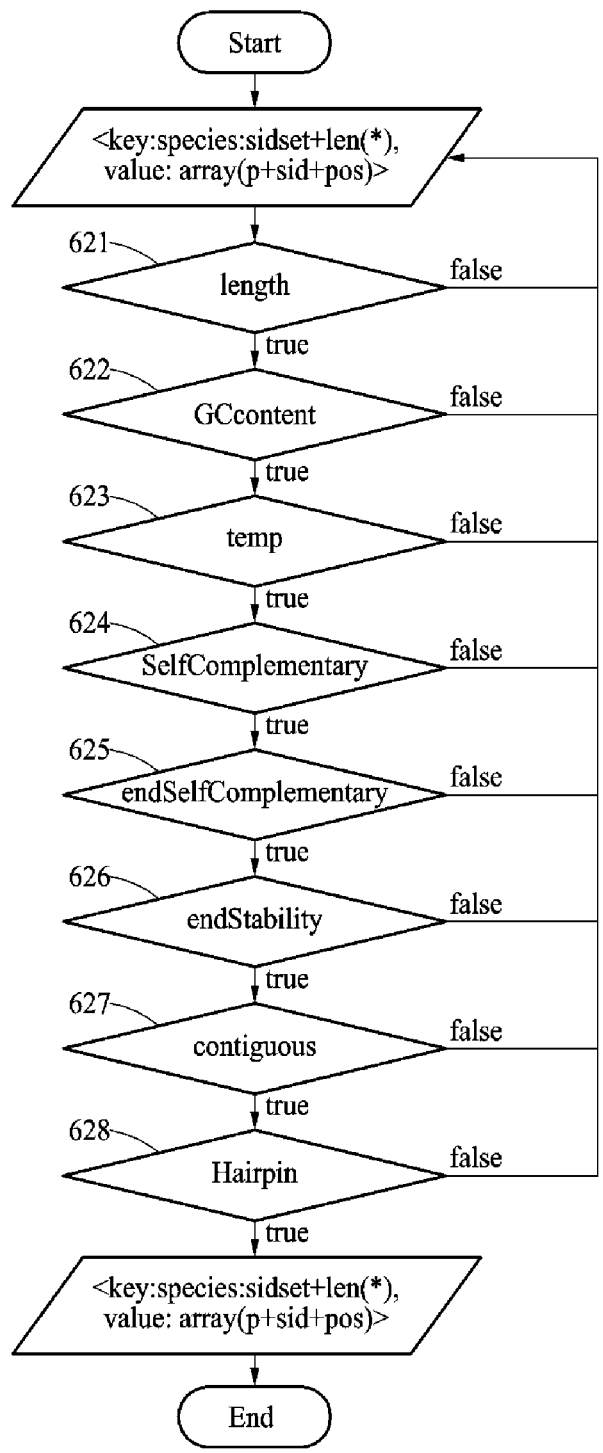
FIG. 7 is a flowchart illustrating an example of a single filtering operation performed in operation 620 of FIG. 6.

FIG. 7 is a flowchart illustrating an example of a single filtering operation performed in operation 620 of FIG. 6.

The single filtering operation may be performed by processing a gene-related query language provided by a user, and outputting a result from a cache index in response to filtering condition values being default. Here, in response to the filtering condition values not being default, a primer that does not satisfy a plurality of single filtering conditions applied by the user while searching for a candidate primer from a candidate primer index may be removed.

Referring to FIG. 7, in operations 621 through 628, a length, a temperature, a guanine-cytosine (GC) content, a self-complementarity, a 3' end self-complementarity, consecutive bases, an end stability, and a hairpin are verified sequentially as the single filtering conditions to remove a primer that does not satisfy the single filtering conditions provided by the user.

Respective values of the single filtering conditions may be defined by the user. To calculate the temperature in particular, various equations or formulas may be suggested. A most well-known accurate equation, for example, that is published as "the thermodynamics of DNA structural motifs" in Annu. Rev. Biophys. Biomol. Struct., 33, 415-440 p, by SantaLucia Jr, J. and Hicks, D. (2004), is applied herein. Similarly, to calculate the end stability, a most accurate method, for example, a nearest neighbor thermodynamics method, is applied herein.

Hereinafter, the pair filtering operation performed in operation 630 described with reference to FIG. 6 will be described in greater detail with reference to FIG. 8.

Figure 8:
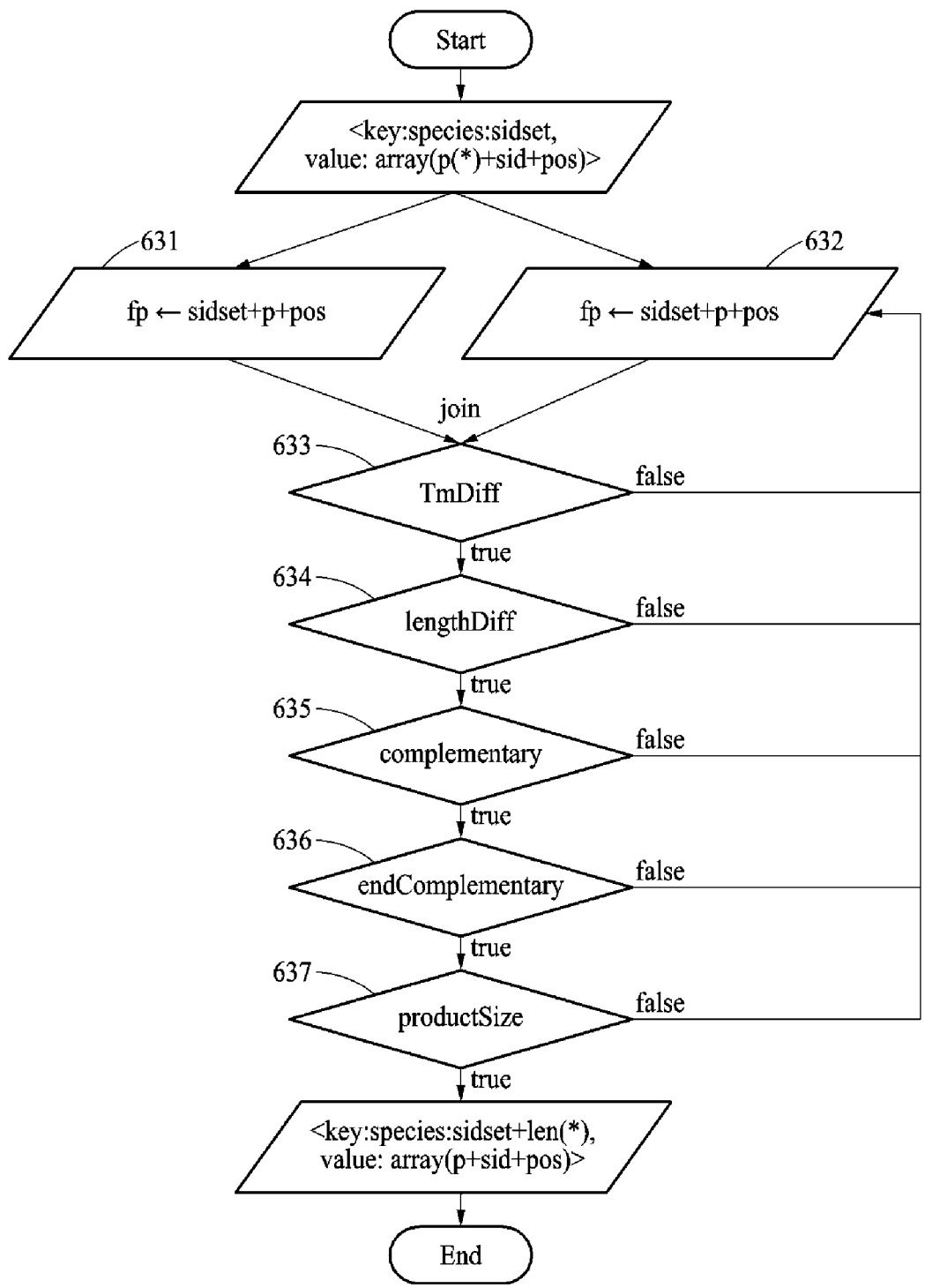
FIG. 8 is a flowchart illustrating an example of a pair filtering operation performed in operation 630 of FIG. 6.

FIG. 8 is a flowchart illustrating an example of a pair filtering operation performed in operation 630 of FIG. 6.

The pair filtering operation may be performed by applying a plurality of pair filtering conditions provided by a user to primers remained through the single filtering operation described with reference to FIG. 7, and designing primers obtained through the pair filtering conditions as a primer pair.

Referring to FIG. 8, in operations 631 and 632, candidate primers are divided into two sets—a forward primer set and a reverse primer set, and calculations or computations are performed on the two sets.

In operations 633 through 637, five pair filtering conditions are applied to primer pairs.

In operations 633 through 637, the pair filtering conditions, for example, a temperature difference, a length difference, a generated product length, a pair-complementarity, and a 3' end pair-complementarity, are verified sequentially. Respective values of the pair filtering conditions may be defined by the user.

FIG. 9 is a flowchart illustrating an example of the sorting operation performed in operation 640 of FIG. 6. Referring to FIG. 9, in operation 641, respective penalties of primer pairs obtained through the pair filtering operation described with reference to FIG. 8 are calculated. That is, a penalty of each of the primer pairs is calculated by a sum of a forward primer penalty and a reverse primer penalty.

In operation 642, when the penalties of the primer pairs are calculated, top (or highest-rank) primer pairs having a highest penalty in a same sidset group are output to a webpage along with a probe satisfying a corresponding position condition. That is, a search for a probe positioned between a forward primer and a reverse primer of an optimal primer pair is performed, and the retrieved probe is output to the webpage along with the top primer pairs having the highest penalty in the same sidset group. That is, in operation 642, whether a position of the probe retrieved from the probe index corresponds to a position condition associated with the forward primer and the reverse primer of the primer pair.

FIGS. 10A through 10D are captured images of examples of output results according to an example embodiment. FIGS. 10A through 10D illustrate a method of outputting a final result.

Figure 10A:
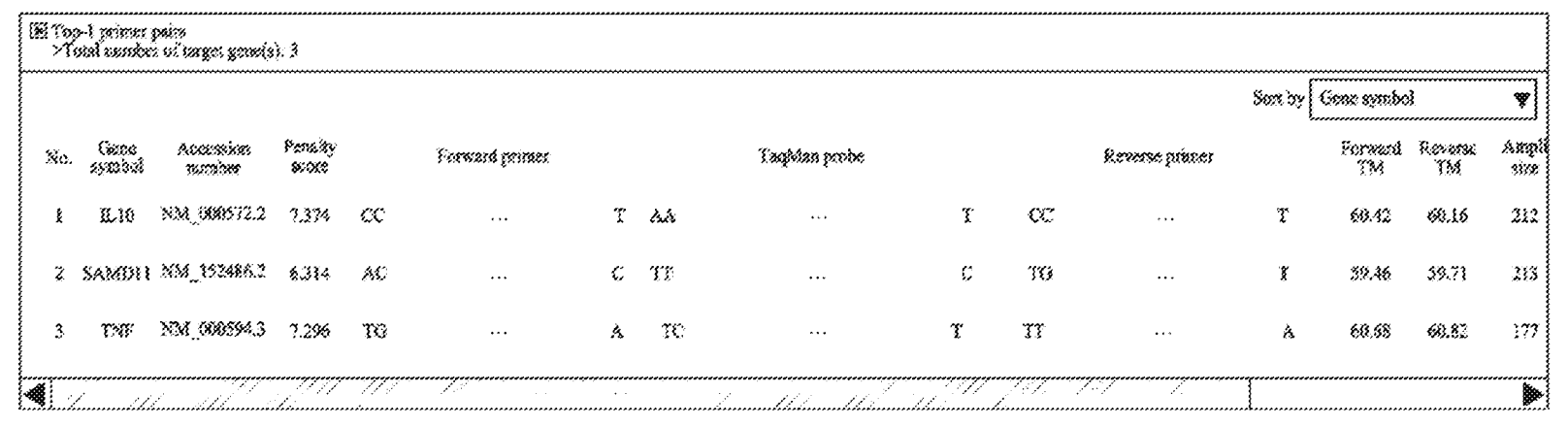

FIG. 10A illustrates probes and top (or top-1 as illustrated) primer pairs to be attached to a single target sequence and satisfying single and/or pair filtering conditions input by a user. FIG. 10B illustrates top primer pairs to be attached to multiple target sequences and satisfying single and/or pair filtering conditions input by a user.

FIG. 10C illustrates a result that is output in response to queries based on which primer pairs satisfying strict single and/or pair filtering conditions input by a user are not retrieved. FIG. 10D illustrates a result that is output in response to queries based on which valid candidate primers are not retrieved due to the valid candidate primers not being in a corresponding index.

Here, in a case that the primer pairs satisfying the single and/or pair filtering conditions input by the user are not retrieved or found, and that the valid candidate primers are not present because a query language input by the user does not correspond to the index, an interactive interface that allows the user to immediately correct the query language and a corresponding condition from a display of the webpage and perform a re-search using the corrected query language and the corrected condition may be provided.

In addition, when all the processes described in the foregoing are completed, a function that allows the user to receive a search result through an e-mail address input by the user may also be provided.

A method of simultaneously designing a valid primer set and a valid probe set that satisfy a specificity condition to detect multiple target genes is described herein according to example embodiments. However, a scope of example embodiments is not limited to the provided example embodiments described herein, and thus modifications and changes may be made within a range obvious to a person having ordinary skill in the art.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner, and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

The components described in the example embodiments of the present disclosure may be achieved by hardware components including at least one DSP (Digital Signal Processor), a processor, a controller, an ASIC (Application Specific Integrated Circuit), a programmable logic element such as an FPGA (Field Programmable Gate Array), other electronic devices, and combinations thereof. At least some of the functions or the processes described in the example embodiments of the present disclosure may be achieved by software, and the software may be recorded on a recording medium. The components, the functions, and the processes described in the example embodiments of the present disclosure may be achieved by a combination of hardware and software.

The processing device described herein may be implemented using hardware components, software components, and/or a combination thereof. For example, the processing device and the component described herein may be implemented using one or more general-purpose or special purpose computers, such as, for example, a processor, a controller and an arithmetic logic unit (ALU), a digital signal processor, a microcomputer, a field programmable gate array (FPGA), a programmable logic unit (PLU), a microprocessor, or any other device capable of responding to and executing instructions in a defined manner. The processing device may run an operating system (OS) and one or more software applications that run on the OS. The processing device also may access, store, manipulate, process, and create data in response to execution of the software. For purpose of simplicity, the description of a processing device is used as singular; however, one skilled in the art will be appreciated that a processing device may include multiple processing elements and/or multiple types of processing elements. For example, a processing device may include multiple processors or a processor and a controller. In addition, different processing configurations are possible, such as parallel processors.

The software may include a computer program, a piece of code, an instruction, or some combination thereof, to independently or collectively instruct or configure the processing device to operate as desired. Software and data may be embodied permanently or temporarily in any type of machine, component, physical or virtual equipment, computer storage medium or device, or in a propagated signal wave capable of providing instructions or data to or being interpreted by the processing device. The software also may be distributed over network coupled computer systems so that the software is stored and executed in a distributed fashion. The software and data may be stored by one or more non-transitory computer readable recording mediums. The non-transitory computer readable recording medium may include any data storage device that can store data which can be thereafter read by a computer system or processing device. Examples of the non-transitory computer readable recording medium include read-only memory (ROM), random-access memory (RAM), CD-ROMs, magnetic tapes, floppy disks, optical data storage devices. Also, functional programs, codes, and code segments that accomplish the examples disclosed herein can be easily construed by programmers skilled in the art to which the examples pertain based on and using the flow diagrams and block diagrams of the figures and their corresponding descriptions as provided herein.

The methods according to the above-described example embodiments may be recorded in non-transitory computer-readable media including program instructions to implement various operations of the above-described example embodiments. The media may also include, alone or in combination with the program instructions, data files, data structures, and the like. The program instructions recorded on the media may be those specially designed and constructed for the purposes of example embodiments, or they may be of the kind well-known and available to those having skill in the computer software arts. Examples of non-transitory computer-readable media include magnetic media such as hard disks, floppy disks, and magnetic tape; optical media such as CD-ROM discs, DVDs, and/or Blue-ray discs; magneto-optical media such as optical discs; and hardware devices that are specially configured to store and perform program instructions, such as read-only memory (ROM), random access memory (RAM), flash memory (e.g., USB flash drives, memory cards, memory sticks, etc.), and the like. Examples of program instructions include both machine code, such as produced by a compiler, and files containing higher level code that may be executed by the computer using an interpreter. The above-described devices may be configured to act as one or more software modules in order to perform the operations of the above-described example embodiments, or vice versa.

What is claimed is:

1. A method of performing a quantitative polymerase chain reaction (PCR) process, comprising:
    designing a valid primer pair and a probe satisfying a specificity condition from a deoxyribonucleic acid (DNA) sequence database, by, via a processor of a computing device:
        receiving a query language associated with a gene and primer-related filtering conditions,
        searching for a key having at least one base sequence corresponding to the query language in a genetic information index comprising:
            a two hash-structured index comprising unique gene information, the unique gene information comprising at least one of a GenBank accession number and a consensus coding sequence (CODS) identification (ID) of National Center for Biotechnology Information (NCBI) (NCBI CCDS ID);
            a four list-structured index comprising duplicated gene information, the duplicated gene information comprising at least one of an NCBI gene symbol, an NCBI gene ID, a GenBank alias, and a keyword;
            a single list-structured index comprising the unique gene information and the duplicated gene information; and
            a plurality of keys associated with the unique gene information and the duplicated gene information, each of the plurality of keys associated with a value comprising at least one sequence identifier (sids) associated with the unique gene information and the duplicated gene information,
        determining at least one candidate primer from a candidate primer set index and at least one candidate probe from a candidate probe set index, wherein the candidate primer and the probe satisfy the specificity condition and are associated with the at least one sequence identifier (sids) of the at least one base sequence, and
        filtering the at least one candidate primer based on the gene and primer-related filtering conditions;
    providing to a webpage information about a primer pair satisfying the query language and the filtering conditions based on a result of the filtering; and
    performing the qPCR process using the primer pair satisfying the query language and the filtering conditions.

2. The method of claim 1, wherein the candidate primer set index is a hash-structured index including a key field and a value field, wherein the key field is in a form of species: sidset+len(*) in which len denotes a primer length and * denotes a reverse primer, and the value field is in a form of primer+sid+pos including a primer sequence and position information (pos).

3. The method of claim 1, wherein the candidate primer set index is provided in advance through a Hadoop-based offline operation for the deoxyribonucleic acid (DNA) sequence database.

4. The method of claim 3, wherein
    the candidate primer set index is generated by extracting a candidate primer set satisfying an applied minimum number of the filtering conditions from the DNA sequence database through a Hadoop distribution algorithm, and
    at least one candidate primer is determined by extracting a candidate primer passing a homology test from the extracted candidate primer set, wherein the homology test compares the extracted candidate primer set to non-target sequences through the Hadoop distribution algorithm and removes, from the extracted candidate primer set, a candidate primer having a 5' end with a preset number or greater number of mismatches and having a remaining 3' end or a candidate primer only having a preset number of mismatches.

5. The method of claim 1, further comprising:
    filtering the at least one candidate probe based on probe-related filtering conditions; and
    searching for a probe suited to a position condition associated with the primer pair from candidate probes obtained through the probe-related filtering.

6. The method of claim 1, in response to the primer-related filtering conditions corresponding to a default value, further comprising: searching for at least one primer pair from a cache primer pair index based on the identifier of the at least one base sequence.

7. The method of claim 6, wherein the cache primer pair index is a hash-structured index comprising top primer pairs calculated in advance with respect to each target sequence, and comprises a key and a value, wherein the key and the value are arranged in a form of species:top:sidset, including a top primer pair associated with a sidset, and in a form of sid+f.p+r.p+f.pos+r.pos, including a sequence identifier, a forward primer penalty, a reverse primer penalty, a forward primer position, and a reverse primer position, respectively.

8. The method of claim 1, wherein the filtering comprises:
    filtering the at least one candidate primer based on a single filtering condition among the filtering conditions; and
    designing the primer pair from candidate primers satisfying the single filtering condition based on a pair filtering condition among the filtering conditions.

9. The method of claim 1, wherein the filtering comprises: removing a primer not satisfying a single filtering condition by verifying in order a length, a temperature, a guanine-cytosine (GC) content, a self-complementarity, a 3' end self-complementarity, consecutive bases, an end stability, and a hairpin of the single filtering condition.

10. The method of claim 1, wherein the filtering comprises: removing a primer not satisfying a pair filtering condition by verifying in order a temperature difference, a length difference, a generated product length, a pair-complementarity, and a 3' end pair-complementarity of the pair filtering condition.

11. The method of claim 1, in response to a presence of multiple primer pairs satisfying the filtering conditions, further comprising: sorting the multiple primer pairs by each same sidset group.

12. The method of claim 11, wherein the sorting comprises: calculating, as a penalty of each of primer pairs passing a pair filtering process, a sum of a forward primer penalty and a reverse primer penalty of each of the primer pairs.

13. The method of claim 12, in response to the penalty being calculated for each of the primer pairs, further comprising: outputting, based on the penalty calculated for each of the primer pairs, top primer pairs in a same sidset group to the webpage along with probes satisfying position conditions associated with the top primer pairs.

14. The method of claim 1, wherein the gene and primer-related filtering conditions comprises single and/or pair filtering conditions input by a user, and the method further comprising:
   outputting each of top primer pairs of the at least one candidate primer, wherein each of the top primer pairs attaches to a single target sequence and satisfies the single and/or pair filtering conditions;
   outputting top primer pairs of the at least one candidate primer, wherein each of the top primer pairs attaches to multiple target sequences and satisfies the single and/or pair filtering conditions;
   outputting queries based on which searches for primer pairs satisfying the single and/or pair filtering conditions are not performed; and
   outputting queries based on which searches for valid candidate primers are not performed due to the valid candidate primers not being in the candidate primer set index.

15. The method of claim 1, wherein the gene and primer-related filtering conditions comprises single and/or pair filtering conditions input by a user, and the method further comprising:
   in response to a presence of probes and top primer pairs to be attached to a single target sequence and satisfying the single and/or pair filtering conditions, providing gene information, a primer pair sequence, a probe sequence, a temperature, an amplicon size, and a position;
   in response to a presence of top primer pairs to be attached to multiple target sequences and satisfying the single and/or pair filtering conditions, providing gene information, a primer pair sequence, a temperature, an amplicon size, and a position;
   in response to an absence of a primer pair satisfying the single and/or pair filtering conditions, providing gene information, conditions of which a value is to be changed, a value input by the user, and a value to be corrected; and
   in response to an absence of a valid candidate primer due to the valid candidate primer not being in a corresponding index, providing a query language without a result and a re-search guideline.

16. The method of claim 15, in response to the absence of the primer pair satisfying the single and/or pair filtering conditions input by the user and in response to the absence of the valid candidate primer due to the valid candidate primer not being in the corresponding index, further comprising: providing an interactive interface to obtain an accurate search result by allowing the user to immediately correct a query language and a condition from a result display and perform a re-search using the corrected query language and the corrected condition.

17. The method of claim 1, wherein the candidate probe set index is a hash-structured index including a key field and a value field, wherein the key field is in a form of species: taqman+sidset, and the value field is in a form of probe+sid+pos including a probe sequence and position information (pos).

* * * * *